(12) United States Patent
Allegrini et al.

(10) Patent No.: US 7,982,062 B2
(45) Date of Patent: Jul. 19, 2011

(54) PROCESS FOR THE PREPARATION OF CHOLANIC ACIDS

(75) Inventors: Pietro Allegrini, San Donato Milanese (IT); Tiziano Scubla, Pasian Di Prato (IT); Fausto Gorassini, Udine (IT); Andrea Finco, Pordenone (IT)

(73) Assignee: Dipharma Francis s.r.l., Baranzate (IT)

( * ) Notice: Subject to any disclaimer, the term of this patent is extended or adjusted under 35 U.S.C. 154(b) by 970 days.

(21) Appl. No.: 11/853,632

(22) Filed: Sep. 11, 2007

(65) Prior Publication Data

US 2008/0064888 A1    Mar. 13, 2008

(30) Foreign Application Priority Data

Sep. 12, 2006   (IT) .............................. MI2006A1735

(51) Int. Cl.
*C07J 9/00* (2006.01)

(52) U.S. Cl. ........................ 552/548; 552/549; 552/551

(58) Field of Classification Search .................. 514/170; 552/548, 549, 551
See application file for complete search history.

(56) References Cited

U.S. PATENT DOCUMENTS

| 2,758,120 A * | 8/1956 | Ziegler et al. .................. 552/551 |
| 3,006,927 A | 10/1961 | Liebig et al. |
| 3,965,131 A * | 6/1976 | Wiele et al. .................... 552/551 |
| 4,022,806 A * | 5/1977 | Frost et al. ..................... 552/551 |
| 5,349,074 A * | 9/1994 | Bonaldi ......................... 552/551 |
| 5,429,940 A | 7/1995 | Urakami et al. |

OTHER PUBLICATIONS

Karlaganis et al., "Determination of bile acids by capillary gas-liquid chromatography-mass spectrometry". Ital. J. Gastroenterol., vol. 12, pp. 121-123, 1980.*

Laatikainen et al., "Determination of serum bile acids by glass capillary gas-liquid chromatography". Clinica Chimica Acta, vol. 64, pp. 63-68, 1975.*

Search Report Issued in the Corresponding European Application No. 07 11 3916 on Apr. 18, 2008.

Hyodeoxycholic Acid webpage downloaded from www.cdyg.com/template/hyodeoxycholic_acid.htm on Nov. 28, 2010, filed herewith as Exhibit A.

Hyodesoxycholic Acid webpage downloaded from www.standard-substance.com/products/Plant-Modifier/Hyod..., on Nov. 28, 2010, filed herewith as Exhibit B.

The webpage "C9377 Chenodeoxycholic acid >95%," downloaded from www.sigmaaldrich.com/catalog..., on Nov. 29, 2010, 1 page, filed herewith as Exhibit C.

The webpage "D2510 Deoxycholic acid >99% (TLC and titration)," downloaded from www.sigmaaldrich.com/catalog..., Nov. 29, 2010, 2 pages, filed herewith as Exhibit D.

T.F. Gallagher et al., "Partial Oxidation of Hyodesoxycholic Acid," pp. 365-370, (1946), downloaded from www.jbc.org on Nov. 28, 2010.

* cited by examiner

*Primary Examiner* — Barbara P Badio
(74) *Attorney, Agent, or Firm* — Griffin & Szipl, P.C.

(57) ABSTRACT

A process for the preparation of high purity cholanic acids, typically in purity equal to or higher than 99%.

18 Claims, No Drawings

PROCESS FOR THE PREPARATION OF CHOLANIC ACIDS

This application claims priority from Italian Patent Application No. MI2006A001735 filed Sep. 12, 2006, the entire disclosure of which is incorporated herein by reference.

FIELD OF THE INVENTION

The present invention relates to a novel process for the preparation of high purity cholanic acids, in particular chenodeoxycholic and hyodeoxycholic acids, from swine bile. Such acids are useful both as biologically active pharmaceutical ingredients and intermediates for the preparation of pharmaceutical ingredients.

TECHNOLOGICAL BACKGROUND

A number of processes for the preparation of hyodeoxycholic and chenodeoxycholic acids starting from swine bile are known, for example those disclosed in U.S. Pat. No. 2,758,120, U.S. Pat. No. 3,006,927 and U.S. Pat. No. 5,349,074. The method's known to date are however complex, hence poorly suited to an industrial scale, nor they afford the desired products in sufficient purity for the direct use in therapy or as intermediates in the preparation of other active pharmaceuticals such as ursodeoxycholic acid.

SUMMARY OF THE INVENTION

A novel process has now been found for the separation of cholanic acids, in particular chenodeoxycholic and hyodeoxycholic acids, from swine bile, comprising:
a) hydrolysis of swine bile with an alkali hydroxide;
b) recovery of a crude mixture of cholanic acids salts;
c) separation of these by chromatography; and
d) recovery of the acids in the purified form.

The present invention provides a simple, industrially applicable process for the recovery of the desired cholanic acids, in particular hyodeoxycholic and chenodeoxycholic acids, in highly pure form which makes them suited both as pharmaceutical active principles and as intermediates for the preparation of other pharmaceutical active principles.

DETAILED DISCLOSURE OF THE INVENTION

An object of the invention is a process for the preparation of high purity bile acids, in particular hyodeoxycholic acid and chenodeoxycholic acid, comprising:
a) hydrolysis of swine bile with an alkali hydroxide;
b) recovery of the crude mixture of cholanic acids salts;
c) separation of these by chromatography; and
d) recovery of the acids in the purified form.

The swine bile used as starting material can have water content ranging from to 80%, and contains cholanic acids, in particular hyodeoxycholic, chenodeoxycholic and hyocholic acids, in the form of taurine conjugates. Alternatively, concentrated swine bile can be used, which is then diluted to a total solid content (approximately 11%-12%) similar to that of fresh bile.

Hydrolysis of cholanic acids can be carried out by treatment with alkali hydroxides, typically sodium or potassium hydroxides, preferably sodium hydroxide, in amounts approximately ranging from 5% to 20% of the bile weight, preferably approximately from 8% to 12%. The reaction can be carried out by refluxing the mixture for a time from 10 to 30 hours, preferably from 18 to 22 hours.

The cholanic acids crude mixture, in the form of the corresponding alkali salts, can be recovered by successive extractions, typically two, with a solvent at controlled pH. In particular, the mixture is acidified to pH approximately ranging from 3 to 6, preferably from 4 to 5, with a mineral acid, for example hydrochloric acid, then extracted with a water-immiscible solvent, typically an ester solvent, such as ethyl acetate, butyl acetate or isopropyl acetate, preferably ethyl acetate. The organic phase containing the products as the free acids and some by-products is then treated with water and the mixture is alkalinized to pH approximately ranging from 9 to 13, preferably approximately from 10 to 12, by adding a sodium hydroxide solution. The cholanic acids mixture, in the form of the corresponding sodium salts, is then extracted in the aqueous phase while by-products remain in the organic phase. The aqueous phase is separated and directly used in the subsequent step.

The separation of cholanic acids, i.e. hyodeoxycholic acid and chenodeoxycholic acid, in the salified form, can be carried out by means of chromatographic procedures, for example by elution on a column containing a stationary phase. The stationary phase can be for example a ion exchange resin, e.g. a strong cationic, weak cationic, strong anionic, weak anionic resin, or an adsorbing resin, such as Amberlite®, Polyclar®, Sephadex®, a DIAION® resin, particularly DIAION® HP 20 SS. The mobile phase can be water, a $C_1$-$C_6$ alkanol, preferably methanol, or mixtures thereof. The elution can be isocratic o in gradient, and preferably is in water-methanol gradient, from 100% water to 100% methanol. In this manner, fractions containing the pure chenodeoxycholic acid sodium salt and fractions containing a mixture of hyodeoxycholic and hyocholic acids sodium salts are obtained.

High purity chenodeoxycholic and hyodeoxycholic acids can be recovered from the respective fractions as indicated herein below.

As for chenodeoxycholic acid, fractions are treated with an amount of carboxylic organic acid, e.g. acetic acid, sufficient to liberate the sodium salt and evaporated to a residue. The residue is treated with a hot solvent mixture able to dissolve chenodeoxycholic acid; typically at a temperature approximately ranging from 30 to 60° C., preferably from 45 to 55° C.; for example an ethyl acetate/toluene mixture in a ratio approximately ranging from 1:1 to 1:10, preferably approximately 1:5. The undissolved material is filtered off and the resulting solution is cooled to crystallize chenodeoxycholic acid in a purity equal to or higher than 99%.

As for hyodeoxycholic acid, fractions are evaporated to a residue. The residue is dissolved in water, basified to pH>12 with potassium hydroxide, typically approximately 90%, and treated while hot, at a temperature approximately ranging from 30 to 60° C., preferably from 45 to 55° C., with a magnesium sulphate solution. The formed hyodeoxycholic acid magnesium salt crystallizes and precipitates from the solution upon cooling. The product is suspended in water and recovered by filtration. The mixture is acidified to pH around 2, then treated while hot, typically at a temperature approximately ranging from 30 to 60° C., preferably from 45 to 55° C., with a solvent able to dissolve the hot hyodeoxycholic acid, for example ethyl acetate. The resulting organic phase is separated and cooled to crystallize hyodeoxycholic acid in a purity equal to or higher than 99%.

The invention provides therefore a process for the preparation and the purification of bile acids, in particular hyodeoxycholic acid and chenodeoxycholic acid, which can be obtained in high purity level, typically equal to or higher than 99%, particularly equal to or higher than 99.9%.

The resulting chenodeoxycholic acid can be used as such in therapy, or analogously to hyodeoxycholic acid can be converted to ursodeoxycholic acid, which is used in therapy as well, according to known processes.

Example 1000 g of swine bile are refluxed for 20 hours with 100 g of sodium hydroxide. The mixture is cooled to a temperature of 70° C. and added with 240 g of ethyl acetate and 6 g of hydrogen peroxide. The formed pale green mixture is acidified to pH 4-5 with 130 g of 37% hydrochloric acid. The two phases are separated. The organic phase is added with 140 g of water and the solution is alkalinised to pH 11 with 67 g of 35% sodium hydroxide.

The aqueous phase is separated from the organic phase by means of a separatory funnel. The aqueous phase containing the salified cholanic acids is eluted on a DIAION® HP 20SS resin, using a solvent gradient to afford the separation (water-water\methanol-methanol).

Elution on resin provides the complete separation of chenodeoxycholic acid sodium salt from a mixture containing hyocholic and hyodeoxycholic acids sodium salts.

The fractions containing chenodeoxycholic acid salt are combined, treated with an amount of acetic acid sufficient to liberate the sodium salt and evaporated to a residue. The resulting solid is then dissolved in an ethyl acetate/toluene 1:5 mixture. The residue insoluble while hot is filtered off and the resulting solution is cooled to promote crystallization of the product. The formed precipitate is filtered and dried under vacuum. 20 g of chenodeoxycholic acid are obtained, having 99.9% HPLC purity.

The fractions containing the mixture of hyodeoxycholic and hyocholic acids sodium salts are evaporated under reduced pressure, the residue is taken up in 500 g of water, mechanically stirred and heated to inner temperature of 50° C. A solution of 90% potassium hydroxide is added to pH 12. After that, a magnesium sulphate aqueous solution is dropped therein. The solution is cooled, the formed precipitate is filtered and dried at 50-60° C. under vacuum. The precipitate consists of hyodeoxycholic acid magnesium salt, which is placed in a reactor together with 200 g of water and 600 g of ethyl acetate; the mixture is heated to inner temperature of 55° C. and added with 35% sulfuric acid to pH 2. The phases are separated, and the organic phase is cooled to 0/−5° C. The formed white precipitate is filtered and dried under vacuum at 50° C. 24 g acid hyodeoxycholic are obtained, with 99.9% HPLC purity.

The invention claimed is:

1. A process for the preparation of high purity hyodeoxycholic acid and chenodeoxycholic acid, comprising the steps of:
   (a) hydrolysis of swine bile with an alkali hydroxide;
   (b) recovery of a crude mixture of cholanic acids salts by successive extractions at controlled pH;
   (c) separation of cholanic acid salts by chromatography; and
   (d) recovery of the hyodeoxycholic acid and the chenodeoxycholic acid in a purified form.

2. A process as claimed in claim 1, wherein in step (b), in a first extraction, the mixture is acidified to a pH approximately ranging from 3 to 6.

3. A process as claimed in claim 2, wherein an extracting solvent employed in step (b) is an ester solvent.

4. A process as claimed in claim 1, wherein in step (b), the cholanic acids mixture, in the form of the corresponding sodium salt, is subjected to a subsequent extraction in an aqueous phase.

5. A process as claimed in claim 1, wherein in step (c), the stationary phase in the chromatography is an ion exchange resin or an adsorbing resin.

6. A process as claimed in claim 1, wherein in step (c), in the chromatography the mobile phase is water, a $C_1$-$C_6$ alkanol or mixtures thereof.

7. A process as claimed in claim 6, wherein elution is in a water-methanol gradient, ranging from 100% water to 100% methanol.

8. A process as claimed in claim 1, wherein in step (d), chenodeoxycholic acid is recovered by a process comprising the steps of
   i. treatment with a carboxylic acid;
   ii. treatment with a solvent mixture that dissolves chenodeoxycholic acid at a temperature approximately ranging from 30 to 60° C.; and
   iii. crystallization of the chenodeoxycholic acid from the solvent mixture.

9. A process as claimed in claim 1, wherein in step (d), hyodeoxycholic acid is recovered by a process comprising the steps of
   i. formation of a magnesium salt of hyodeoxycholic acid;
   ii. treatment with a solvent that dissolves hyodeoxycholic acid at a temperature approximately ranging from 30 to 60° C.; and
   iii. crystallization of the hyodeoxycholic acid from the solvent.

10. A process as claimed in claim 1, wherein the purified form of the hyodeoxycholic acid and of the chenodeoxycholic acid has a purity deuce equal to or higher than 99%.

11. A process for the preparation of high purity hyodeoxycholic acid and chenodeoxycholic acid, comprising the steps of:
   (a) hydrolysis of swine bile with an alkali hydroxide;
   (b) recovery of a crude mixture of cholanic acids salts by successive extractions at controlled pH;
   (c) separation of cholanic acid salts by chromatography; and
   (d) recovery of the hyodeoxycholic acid and chenodeoxycholic acid in a purified form, wherein chenodeoxycholic acid is recovered by a process comprising the steps of
      i. treatment with a carboxylic acid;
      ii. treatment with a solvent mixture that dissolves chenodeoxycholic acid at a temperature approximately ranging from 30 to 60° C., wherein the solvent mixture consists of ethyl acetate and toluene; and
      iii. crystallization of the chenodeoxycholic acid from the solvent mixture.

12. A process as claimed in claim 11, wherein the chenodeoxycholic acid recovered has a purity degree equal to or higher than 99%.

13. A process for the preparation of high purity hyodeoxycholic acid and chenodeoxycholic acid, comprising the steps of:
   (a) hydrolysis of swine bile with an alkali hydroxide;
   (b) recovery of a crude mixture of cholanic acids salts by successive extractions at controlled pH;
   (c) separation of cholanic acid salts by chromatography; and (d) recovery of the hyodeoxycholic acid and the chenodeoxycholic acid in a purified form, wherein hyodeoxycholic acid is recovered by a process comprising the steps of
  i. formation of a magnesium salt of hyodeoxycholic acid;
  ii. treatment with a solvent that dissolves hyodeoxycholic acid at a temperature approximately ranging from 30 to 60° C., wherein the solvent is ethyl acetate; and
  iii. crystallization of the hyodeoxycholic acid from the solvent.

14. A process as claimed in claim 13, wherein the hyodeoxycholic acid recovered has a purity degree equal to or higher than 99%.

15. A process as claimed in claim 1, wherein the cholanic acid salts are sodium salts.

16. A process as claimed in claim 15, wherein in step (c), the cholanic acid salts are separated in fractions by chromatography on an ion exchange resin or the cholanic acid salts are separated in fractions by chromatography on an absorbing resin.

17. A process as claimed in claim 16, wherein the cholanic acid salts separated by chromatography in step (c) include a first fraction containing chenodeoxycholic acid sodium salt and a second fraction containing a mixture of hyodeoxycholic acid sodium salt and hyocholic acids sodium salts.

18. A process for the preparation and use of high purity hyodeoxycholic acid and chenodeoxycholic acid, comprising the steps of:
  (a) hydrolysis of swine bile with an alkali hydroxide;
  (b) recovery of a crude mixture of cholanic acids salts by successive extractions at controlled pH;
  (c) separation of cholanic acid salts by chromatography;
  (d) recovery of the hyodeoxycholic acid and the chenodeoxycholic acid in a purified form; and
  (e) conversion of the recovered hyodeoxycholic acid, or the recovered chenodeoxycholic acid, or the recovered hyodeoxycholic acid and chenodeoxycholic acid, to ursodeoxycholic acid.

* * * * *